United States Patent [19]

Chang

[11] Patent Number: 5,789,490
[45] Date of Patent: Aug. 4, 1998

[54] AMINE CAPPED POLYETHERS AND PROCESS FOR PRODUCING SAME

[75] Inventor: Dane Chang, Sugar Land, Tex.

[73] Assignee: The Dow Chemical Company, Midland, Mich.

[21] Appl. No.: 720,850

[22] Filed: Oct. 3, 1996

Related U.S. Application Data

[60] Provisional application No. 60/004,773 Oct. 4, 1995.

[51] Int. Cl.⁶ .................... C07C 213/00; C07C 213/02
[52] U.S. Cl. .................... 525/403; 525/409; 528/425; 528/483; 528/492
[58] Field of Search ........................ 525/403, 409; 528/425, 483, 492

[56] References Cited

U.S. PATENT DOCUMENTS

| | | |
|---|---|---|
| 3,151,115 | 9/1964 | Moss et al. |
| 3,270,059 | 8/1966 | Winderl et al. |
| 3,383,417 | 5/1968 | Lichtenwalter |
| 3,520,933 | 7/1970 | Adam et al. |
| 3,654,370 | 4/1972 | Yeakey |
| 4,014,933 | 3/1977 | Boettger et al. |
| 4,111,840 | 9/1978 | Best ........................ 252/432 |
| 4,123,462 | 10/1978 | Best |
| 4,152,353 | 5/1979 | Habermann |
| 4,206,149 | 6/1980 | Slaugh |
| 4,400,539 | 8/1983 | Gibson et al. ........................ 564/480 |
| 4,404,405 | 9/1983 | Winters ........................ 564/482 |
| 4,588,840 | 5/1986 | Gurgiolo ........................ 564/443 |
| 4,634,502 | 1/1987 | Callahan et al. ........................ 204/23 |
| 4,647,701 | 3/1987 | Gibson ........................ 564/479 |
| 4,701,434 | 10/1987 | Köll ........................ 502/230 |
| 4,772,750 | 9/1988 | Habermann ........................ 564/472 |
| 4,775,696 | 10/1988 | Prada-Silva et al. ........................ 518/714 |
| 4,855,275 | 8/1989 | Suresh et al. ........................ 502/353 |
| 4,855,505 | 8/1989 | Köll ........................ 564/398 |
| 4,886,772 | 12/1989 | Prada-Silva et al. ........................ 502/200 |
| 4,967,005 | 10/1990 | Smith ........................ 564/475 |
| 4,973,692 | 11/1990 | Burgess et al. ........................ 544/398 |
| 4,973,761 | 11/1990 | Schoenleben et al. ........................ 564/475 |
| 4,975,399 | 12/1990 | Gardner ........................ 502/38 |
| 4,977,266 | 12/1990 | Burgess et al. ........................ 544/398 |
| 4,992,590 | 2/1991 | Cuscurida et al. ........................ 564/505 |
| 5,003,107 | 3/1991 | Zimmerman et al. ........................ 564/475 |
| 5,068,329 | 11/1991 | Burgess et al. ........................ 544/502 |
| 5,068,330 | 11/1991 | Burgess et al. ........................ 544/402 |
| 5,068,444 | 11/1991 | Cuscurida et al. ........................ 564/505 |
| 5,103,062 | 4/1992 | Cuscurida et al. ........................ 564/479 |
| 5,112,364 | 5/1992 | Rath et al. |
| 5,169,971 | 12/1992 | Inomata et al. ........................ 558/338 |
| 5,196,588 | 3/1993 | Burgess et al. ........................ 564/480 |
| 5,202,490 | 4/1993 | Burgess et al. ........................ 564/480 |
| 5,202,491 | 4/1993 | Burgess et al. ........................ 564/480 |
| 5,292,983 | 3/1994 | Sie ........................ 585/733 |
| 5,321,160 | 6/1994 | Hironaka et al. ........................ 564/480 |
| 5,331,101 | 7/1994 | Habermann ........................ 564/480 |
| 5,362,913 | 11/1994 | Knifton et al. ........................ 564/480 |
| 5,424,387 | 6/1995 | Sheehan et al. ........................ 528/61 |
| 5,516,342 | 5/1996 | Cherpeck et al. ........................ 44/347 |

FOREIGN PATENT DOCUMENTS

| | | |
|---|---|---|
| 0 075 940 A1 | 4/1983 | European Pat. Off. |
| 0 181 140 A2 | 5/1986 | European Pat. Off. |
| 0 356 725 A1 | 3/1990 | European Pat. Off. |
| 0 691 157 A1 | 1/1996 | European Pat. Off. |
| 1 569 714 | 6/1980 | United Kingdom |
| 2 066 690 | 7/1981 | United Kingdom |
| 85/00620 A1 | 2/1985 | WIPO |

OTHER PUBLICATIONS

Brennecke, CA 118: 171,631, 1993.
Eckert et. al., CA 125: 309,967, 1996.
Schneider, CA 122: 109,563, 1994.
Ikariya et al., CA 122: 90,470, 1994.
Chemical Abstract 116:87098y (De 4,114,924).
Derwent Abstract 3544S (DT 1943213).
Derwent Abstract 83-804204 (JP 58-159,850).
C. M. Barnes and H. F. Rase, "Ethylendiamine by Low-Pressure Ammonolysis of Monethanlamine", *Ind. Eng. Chem. Prod. Res. Dev.* 1981, 20, 399–407.

*Primary Examiner*—Jeffrey C. Mullis

[57] ABSTRACT

This invention includes catalysts comprising rhenium (atomic number 75), nickel, cobalt, boron and copper and/or ruthenium impregnated on a support material and a process for preparing said catalyst, said process comprising (i) impregnating a mixture of metals comprising rhenium, cobalt, copper and/or ruthenium, boron and nickel on a support material selected from the group consisting of alpha-alumina, silica, silica-alumina, kieselguhrs or diatomaceous earths, and silica-titanias; and (ii) activating said catalyst by heating the catalyst in the presence of hydrogen at an effective temperature preferably in the range of about 150° C. to about 500° C. for a sufficient period preferably of from about 30 minutes to about 6 hours. A further feature of the present invention is a method for producing amine products by the catalytic amination of polyether derivatives including epoxides, monols, diols, polyethers, polyols, alcoholamines, ketones, imino compounds iminoalcohols, ether alcohols, and mixtures thereof, said process comprising contacting said lower polyether derivatives with ammonia and/or reactant amine at an effective temperature preferably from 150° C. to about 500° C. and at an effective pressure preferably from 1000–5000 psig (6895–34.474 kpag) and in the presence of hydrogen and the nickel-rhenium-cobalt-boron-copper and/or ruthenium catalyst as described hereinabove.

40 Claims, No Drawings

AMINE CAPPED POLYETHERS AND PROCESS FOR PRODUCING SAME

This application claims benefit of U.S. Provisional Application No. 60/004,773, filed Oct. 4, 1995.

This invention relates to production of polyetheramines, more specifically production of polyetheramines by reductive amination and the polyetheramines so produced and their uses.

Reductive amination is known in the art and is catalytic amination of aliphatic alkane derivatives such as mono- and poly-hydric alcohols, alcoholamines, and compounds from which these alcohols are derived, including epoxides, ketones and alkyleneimines under reducing conditions, preferably in the presence of hydrogen.

The more desirable amine products are those products in which an amine group replaces the non-amine functional group or groups in the starting material. Heavier, more highly substituted amines and heterocyclic nitrogen compounds can be further synthesized from the preferred polyetheramines. These heavier amines are usually less desirable by-products.

High selectivity has been associated with low conversion rates to product.

Another approach has been to develop catalysts which are more selective while maintaining a rather high conversion rate. For instance, Burgess et al. in U.S. Pat. No. 5,196,588 which is incorporated herein by reference in its entirety disclosed a catalyst having nickel and rhenium in an atom ratio of from 2:1 to 30:1 on a support in an amount corresponding to 3–30 percent by weight of the support material. Various other metals were reported to optionally be present in the catalyst for effects on activity or life of the catalyst. For instance, the presence of boron was reported to have a beneficial effect on the activity of a Ni—Re—B catalyst in Example 7. But in Example 9 boron was reported not to be essential for selectivity or activity, that it "may play a role in the life" of a Ni—Re—Co—B catalyst.

These selective catalysts, however have produced very low yields of amine when the starting material had a high molecular weight such as in the case of polyether alcohols as starting materials.

Other catalysts have produced some polyetheramines but with limited success. For instance, Rath et al. have disclosed in U.S. Pat. No. 5,112,364, which is incorporated herein by reference in its entirety, reductive aminations of certain polyether alcohols with ammonia and certain primary amines. The process is not applied to secondary and tertiary amines. Ammonia was used to reductively aminate a polypropylene glycol in the teachings of Boettger et al U.S. Pat. No. 4,014,933 with a cobalt, nickel and copper catalyst. Other cobalt, nickel and copper catalysts were used to aminate certain polyoxyalkylene polyols with aromatic amines in the teachings of Gurgiolo U.S. Pat. No. 4,588,840.

The use of cobalt, nickel and copper catalysts do not offer the art recognized advantages of nickel/rhenium catalysts which have been developed for improved reductive amination processes.

Polyetheramines produced in accordance with the present invention have many uses. In addition to their use as intermediates for synthesizing other chemical materials, they are utilized, for example, in fungicides, insecticides, other biocides, fuels, detergents, lube (lubrication) oils, dispersants, chelants, defoamers, corrosion inhibitors and others.

SUMMARY OF THE INVENTION

The present invention includes a process for producing polyetheramine products by the catalytic amination of polyether alcohols including arylpolyethers, alkylpolyethers, arylalkylpolyethers, polyether polyols, and mixtures thereof, said process comprising contacting said polyether alcohols with ammonia and/or reactant amine under supercritical conditions in the presence of hydrogen and a catalyst for reductive amination, preferably a nickel-rhenium catalyst.

Another feature of the invention includes the products of such an amination, especially compounds of Formula 1 or Formula 2:

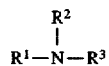
Formula 1

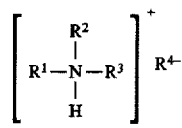
Formula 2 where R1 is a hydroxyalkylpolyether, hydroxyarylpolyether or hydroxyalkylarylpolyether radical of the general formula

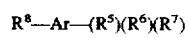
Formula 3a wherein Ar is any aromatic moiety, having at least one aromatic ring, preferably having from 5 to about 7 atoms, preferably carbon, but optionally having at least one heteroatom, preferably nitrogen or oxygen, more preferably nitrogen, including such moieties as 1, 3 diazoles, pyrazoles, pyrazines, pyrimidines, pyridazines, purines, pteridines, thiophenes, oxazones, pyridines, dihydroquinolines, benzoquinolines, diazaanthracenes, naphthalenes, phenyl groups (benzene rings), and the like, and combinations thereof, preferably phenyl groups in which case the preferred structure is

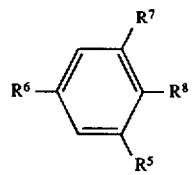
Formula 3b or an alicyclic polyether or alkylalicyclic polyether of the general formula:

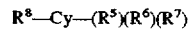
Formula 4a where Cy represents any cyclic structure preferably of at least about 4 atoms, carbon or heteroatoms, said heteroatoms preferably nitrogen or oxygen, preferably at least about 5 atoms, primarily carbon. The Cy structure is exemplified by such moieties as cyclohexane, furan, tetrahydrofuran, dioxolane, pyran, tetrahydropyran, dioxepin, azetidine, dihydropyroles, pyrrolidine, pyrroline, pyrrolidinone, cyclic lactams of from about 5 to about 7 cyclic atoms (preferably from about 4 to about 6 carbon atoms and one nitrogen atom in the ring) and the like and combinations thereof, preferably cyclohexane in which case the molecule conforms to the general formula:

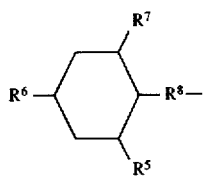

Formula 4b $R^2$ and $R^3$ may be identical or different and are each alkyl, alkylamine, alkyldiamine, or alkylenepolyamine of 1 to about 20 carbon atoms; $R^4$ is any anion e.g. halide, sulfate, carbonate, phosphate, carboxylate;, $R^5$, $R^6$ and $R^7$ may be identical or different and are each hydrogen, hydroxyl, carbonyl, ketone or a hydrocarbon radical of 1 to about 30 carbon atoms, $R^8$ is a polyether chain obtained from an alkylene oxide of 2 to about 8 carbon atoms or a mixture of such alkylene oxides, having from 2 to about 100 alkylene oxide units in the chain; the mean molecular weight Mn of the polyetheramines or polyetheramine derivatives (I) or (II), respectively, being from 00 to 8,000. Ar and Cy are preferably heterocyclic. While compounds of Formulas 1 and 2 are novel, the process also produces such compounds wherein $R^2$ and $R^3$ are optionally hydrogen. These are referred to as compounds of Formulas 1a and 2a respectively. These compounds are novel when Cy or Ar are heterocyclic.

The invention also includes a fuel preferably hydrocarbon fuel, more preferably diesel fuel, aviation fuel or gasoline or a combination thereof. Containing per kg of fuel at least about 1, preferably, from about 1 to about 2000 mg of such polyetheramines or polyetheramine derivatives of Formula 1 or 2, or mixture thereof, preferably Formula. Also included are the same amounts of compounds of Formula 1 or 2 or mixtures thereof in lubricating compositions, corrosion inhibitors, defoaming compositions, dispersants, biocides, defoamers, detergents chelants and combination thereof.

It has been found that under supercritical conditions surprisingly high yields of the desired polyetheramines or derivatives thereof are obtained. These catalysts advantageously permit use of less hydrogen and/or ammonia or amine than is commonly used to achieve the same activity and selectivity with other catalysts; therefore, supercritical conditions are more readily attained. Reducing hydrogen levels is particularly important in obtaining supercritical conditions at conditions of temperature and pressure which are operable and not destructive to the reactants and products of the amination process. The catalysts disclosed in U.S. application Ser. No. 08/459,892 filed Jun. 2, 1995, which is incorporated herein by reference in its entirety are particularly effective for this reason and others.

DETAILED DESCRIPTION OF THE INVENTION

Reductive amination of alcohols involves a reaction between ammonia and/or amines and alcohols in the presence of hydrogen gas. The amination process consists of a series of hydrogenation and dehydrogenation catalytic reactions. The mechanism of these various reactions have been extensively discussed in the prior art literature. The first step in the amination process is believed to be a reversible dehydrogenation of the alcohol to give an intermediate carbonyl, commonly an aldehyde. The aldehyde is then converted to an aminoalcohol by reaction with ammonia or an amine present in the reaction mixture. The aminoalcohol then loses water to form the imine. The imine is then hydrogenated to the amine. When the intermediate aldehyde or the imine reacts with amines in the reaction mixture, substituted and heavier amines are formed. Polyether alcohols and substituted alcohols are preferred polyether derivative starting materials for practice of the invention.

The polyether derivatives which can be aminated in the practice of the present invention include polyether derivatives having one or more functional groups replaceable by an amine group. Preferred polyether derivatives include those containing from about 6 to about 500 carbon atoms, more preferably from 10 to about 100 carbon atoms. Preferred arylpolyether derivatives include those having from about 5 to about 500, more preferably from about 10 to about 100 carbon atoms. The functional groups present are suitably on primary, secondary or tertiary carbon atoms, preferably on secondary carbon atoms. At least one of the functional groups present is capable of being replaced by an amine group (e.g. $NH_2$ from ammonia) in the catalytic amination process of the present invention. The preferred replaceable functional groups include hydroxy, aldehyde, carboxyl, ketone or imino groups and combinations of said groups. Illustrative examples of preferred polyether derivative starting materials include polyalkylene glycols, polyalkylene glycols derivatives include these initiated with phenol, pyrrolidine, or other aromatics amines, and/or other derivatives of such polyoxyalkylene alcohols and their derivatives. Preferably, at least one of the functional groups in the starting material is a hydroxy group, ketone, aldehyde, or imino group. When more than one functional group is replaceable, e.g. hydroxy, then if such groups are of similar reactivity, they will be replaced to a roughly equal extent. If, however, they have different reactivities replacement can be selective for the more reactive site or that site can be blocked by means within the skill in the art to control position of the amine group. While amination processes are applicable compounds of various sizes and molecular weights, the process of the invention is particularly useful for compounds having a molecular weight in excess of about 50, preferably in excess of 200. The starting material, however, is advantageously of insufficient molecular weight to interfere with subsequent reaction or use, preferably the starting material, therefore, has a molecular weight less than about 10000, more preferably less than about 5000, most preferably less than about 2000. These molecular weights are those designated Mw in the case of molecules having a distribution of molecular weights. Functional groups which are not commonly replaceable during amination are optionally present in the polyether starting material in combination with or in addition to the replaceable functional groups. For instance, ethers or polyether alcohols are converted to corresponding ether amines or polyetheramines.

Preferred starting materials include polyether alcohols of Formula 5a, 5b, 6a or 6b:

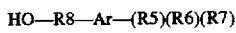

Formula 5a

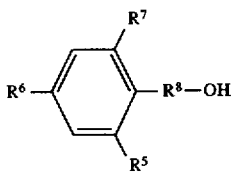

Formula 5b or of cyclohexylpolyethers or alkylcyclohexylpolyethers of the general formula

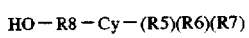

Formula 6a

-continued

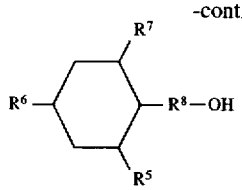

Formula 6b where Cy, Ar, R5, R6, R7 and R8 have the meanings given in the description of Formulas 3a and b and 4a and b.

Selection of a starting material to be used, of course, depends upon the particular amine product desired to be produced. The desired aminated product advantageously differs from the starting material by at least one amine group which replaces at least one non-amine functional group or groups present in the starting material.

The polyether is reacted with ammonia, or optionally and preferably at least one amine in addition to or instead of the ammonia. Any amine which reacts with the polyether derivative under reaction conditions in the presence of the catalyst is suitably used, but preferably the amine is primary or secondary, preferably having from 1 to about 20, more preferably from 1 to about 8 carbon atoms and preferably from 1 to about 10, more preferably from 1 to about 6 nitrogen atoms. Preferred amines include methyl amine, ethylamine, propylamine, butylamine, isopropylamine, ethylenediamine, aniline, piperazine, aminoethylpiperazine, diethylenetriamine, triethylenetetraamine, tetraethylenepentaamine, pentaethylenehexaamine, and the like. In the novel application of the process of the invention to amination of polyether derivatives with secondary amines, the preferred amines include diethylamine, dipropylamine, dibutylamine, diisopropylamine, diisopropanolamine, ethanolamine, diethanolamine, diisobutylamine, preferably diisopropylamine.

This invention utilizes catalysts comprising rhenium (atomic number 75) and nickel, and preferably at least one of cobalt, boron and copper and/or ruthenium impregnated on a support material wherein, preferably, the weight ratio of the nickel to the rhenium is in the range of from 1 to about 30; the weight ratio of the nickel to the cobalt is from about 1 to about 20; the weight ratio of the nickel to the boron is from about 1 to about 20; the weight ratio of the nickel to the copper and/or ruthenium is from about 1 to about 20; and the total nickel, rhenium, cobalt, boron plus copper and/or ruthenium metal present is preferably in the range of from about 5 to about 90 percent by weight of the total (support and metal).

Advantageously, the catalysts are solid catalysts, preferably supported catalysts with the active species provided on the surface of the support through, e.g., coating or impregnation. Support materials are preferably not themselves sufficiently catalytically active to produce high yields of product in a reasonable time. Useful supports are advantageously porous and have surface areas preferably of from about 10 to about 500, more preferably from about 100 to about 300 square meters per gram.

The catalyst is suitably any convenient size or shape, for instance in the form of powders, spherical or conical pellets, extruded strips and the like. The shape of the support usually depends on the shape suited for a particular apparatus used to perform the reaction. Impregnated spherical pellets e.g. ranging in diameter from 1/32 inch to 3/16 inch and extruded strips of a cylindrical-type shape e.g. ranging from 1/32 inch to 1/2 inch in length are among those useful as supports.

While any support material which results in an active amination catalyst is suitably used in the practice of the invention, support materials are not equivalent in their ability to form active Ni—Re catalysts. For example, carbon supported and silica-magnesia supported Ni—Re catalysts using CXC carbon from National Carbon Company even with large surface areas, have reduced catalytic activity in amination reactions. Preferred supports include those based on silicon, aluminum, and/or titanium, preferably based on silica or alumina, particularly alpha-alumina, silica, silica-alumina, kieselguhrs or diatomaceous earths and silica-titania, most preferably silica-based support.

Even the alpha-alumina, silica, silica-alumina, kieselguhrs or diatomaceous earths and silica-titania support materials are not equivalent. Those supports which form more active catalysts are those which yield optimum amination conversions at less severe reaction conditions, e.g., lower reaction temperatures. Therefore, although the catalyst of the invention on most of these supports shows catalytic activity in the amination reaction, some supports are more preferred because they result in a more active catalyst, that are capable of withstanding more extreme reaction conditions, such as higher reaction temperatures and/or exhibit better selectivity for the desired product.

The actual effectiveness of a material as a support in a catalyst is not predictable in advance, but determining effectiveness is within the skill in the art, for instance by methods disclosed in reductive amination catalyst patents such as U.S. Pat. No. 4,123,462 which is hereby incorporated herein by reference in its entirety. Among the types of preferred supports, there appears to be some relationship between catalytic activity and the amount of surface area of the particular support materials. The relationship is believed to be attributable to reactions which occur on the catalyst surface and are, therefore, affected by adsorption-desorption equilibria of the reaction materials. The activity of a catalyst is, therefore, affected, within certain limits, by varying surface area of the supports and other surface properties including support shape, pore size, and pore volume. In general, greater dispersion of the metals on higher surface area active supports produce more active catalysts.

The catalysts include catalysts which contain various other metals in admixture with the nickel and rhenium which do not detrimentally affect catalytic properties. These additional metals, in certain amination processes are optionally used to improve selectivity and activity of the catalyst or extend the activity life and other physical properties of the catalyst. Examples of additional metal components include cobalt, copper, boron, ruthenium, lanthanum, calcium, magnesium, lithium, sodium, potassium, chromium, molybdenum, rubidium, cesium, cerium, iron, silver, zinc, barium, tungsten, uranium, strontium, palladium, titanium, manganese, rhodium and combinations thereof, preferably cobalt, boron, copper, and/or ruthenium.

The catalyst is activated by any procedure wherein the impregnated metal is converted into a catalytically active form. This activation optionally includes alloy formation, proper phase orientation of the metals and/or an adjustment in the oxidation level of the metals. An activation step optionally includes a reduction process within the skill in the art. Often the catalyst is first reduced before effecting the reaction, and then continuously reduced during the course of the reaction to keep the catalyst active and functioning. Insufficient reduction results in depletion of hydrogen at the catalyst surface and resulting decreased reaction.

A preferred activation procedure includes use of a hydrogen atmosphere in contact with the catalyst. The hydrogen is advantageously fed over the catalyst at an elevated temperature, preferably on the order of at least about 150° C., more preferably about 350° C. and preferably less than about 600° C., more preferably less than about 500° C. for periods of from about 30 minutes to about 8 hours, more preferably from about 3 hours to less than about 6 hours. Specific conditions for reduction depend on the particular catalyst composition being activated.

Before or during an activation step, the catalyst is optionally calcined. In a preferred calcining step, the catalyst is heated to temperatures of from about 200° C. to about 500° C. for about 45 minutes to about 3 hours or more if convenient. It is preferred that the calcining be carried out in air.

The drying step previously discussed is optionally replaced by a calcining step or activating step. Alternatively, in such cases drying is considered to take place simultaneously with a calcining and/or activating step.

Nickel—rhenium catalysts suitable for use in the practice of the invention are known in the art and include those disclosed by Best, et al. in U.S. Pat. No. 4,111,840. Preferred catalysts are those disclosed by Burgess et al in U.S. Pat. No. 5,196,588 and those disclosed by Chang et al. in U.S. patent application Ser. No. 08/459,892 filed Jun. 2, 1995, most preferably those disclosed by Chang et al.

The amount of catalyst preferred for use in the practice of the invention depends on many variables including the relative proportions of the reactants, reaction conditions and the degree of conversion and selectivity desired. Moreover, the amount of catalyst also depends on the catalyst itself, e.g., its metal loading, activity and age. Overall, the amount of catalyst used in the process is an amount sufficient to result in the desired reaction.

Reaction conditions of the amination of alkane derivatives are known in the art, but are somewhat dependent on the activity and other characteristics of the catalyst. It has been found, however, that the preferred conditions for alkane and arylalkane derivatives taught in the art are not sufficient for reductive amination of polyether derivatives in high yield.

For reductive amination of polyether derivatives, supercritical conditions are preferred. Those skilled in the art are familiar with the supercritical phase for mixtures of chemicals, but more commonly apply that knowledge to supercritical extractions. Supercritical conditions can be calculated for various mixtures using known formulas or commercially available software e.g. from Aspen and Hysim.

The reaction is run under elevated pressure, advantageously sufficient pressure to maintain desired amounts of hydrogen and ammonia and/or amine in the supercritical phase at a desired temperature. Conveniently the pressure is at least about 20 atmospheres (2026 kPa), preferably at least about 1800 psig (12,413 kPa), more preferably at least about 2400 psig (16,550 kPa), most preferably at least about 3000 psig (20,688 kPa). Preferably the pressure is lower than a pressure which requires unduly heavy equipment or danger, conveniently less than about 400 atmospheres (40,530 pKa).

Preferred temperatures for the reaction depend on the particular starting material, ratios of reactants, and most importantly, the activity of the catalyst used. Temperatures are advantageously at least sufficient to result in supercritical phase and insufficient to result in undesirably increased by-products. Generally, the temperature for the process of the present invention is about 120° C. to about 500° C. Overall, such temperatures are advantageously at least about 120° C., preferably at least about 150° C., more preferably at least about 160° C., most preferably at least about 170° C. Also, to avoid increased by-products, the temperatures are preferably less than about 250° C., more preferably less than about 225° C., most preferably less than about 200° C.

Reactants are optionally fed as a feed stream which is optionally liquid, supercritical fluid or gaseous. Reaction product stream(s) taken from the reaction zone are also optionally liquid, supercritical fluid or gaseous. It is not necessary that the feed stream and the reaction product stream be in the same physical state. For example, a reactant stream is optionally gaseous and a reaction product stream liquid, or vice versa. Feed reactants are suitably supplied in any amount which results in product; conveniently a liquid hourly space velocity (LHSV) (total feed volume divided by volume of reactor containing catalyst per hour) is at least about 0.05 reciprocal hours, advantageously from about 0.05 to about 2, preferably from about 0.1 to about 1.5, more preferably from about 0.25 to about 1, most preferably form about 0.5 to about 0.75 reciprocal hours.

To maintain a given conversion rate, as a reactant polyether derivative feed rates is increased, one or more other process variables are changed; for instance catalytic activity or temperature is increased. Most commonly, a given conversion rate is maintained by an increase in temperature with an increase in e.g. polyether derivatives feed rate. Higher temperatures, however, lead to increased by-products; therefore, the LHSV is balanced with the temperature to achieve the optimum result in each situation.

A feed stream to the amination reaction zone comprises reactant polyether derivative, ammonia and/or amine and hydrogen. Although the reactant polyether derivative optionally contains impurities, polyether derivative.

The feed to the reaction zone also comprises ammonia or amine. Stoichiometrically, one molecular unit of ammonia or amine (primary or secondary) is required per molecular unit of functional group, e.g. hydroxyl, to be replaced. However, the formation of linear compounds is favored by the presence of excess ammonia or amine. Energy consumption gives a practical limit on the amount of ammonia or amine. Thus, the molar ratio of ammonia and/or amine to total polyether derivative is advantageously from at least about 1:1 to about 50:1, preferably from about 1:1 to about 40:1, more preferably from about 1:1 to about 25:1, and most preferably 1:1 to 12:1. One advantage of the present invention is that because of the exceptional selectivity of the catalyst of the present invention, only a relatively small excess of amine and/or ammonia is required. For instance, a molar ratio of 4:1 results in high selectivity for the desired product.

It has been found that increasing the weight ratio of ammonia or amine to the polyether derivative reactant decreases the activity or conversion rate of the reaction in some types of reactors. Excess ammonia or amine is believed to reduce available surface of the catalyst in these instances.

Ammonia or amine employed in the reaction is optionally anhydrous or contains small amounts of water.

Hydrogen is also provided to the amination reaction zone. The amount of hydrogen gas present in the amination process of the present invention is not critical. Advantageously, hydrogen is added in an amount sufficient to maintain the catalyst in an active state. Lower amounts of hydrogen, however, are preferred for maintaining a supercritical state. A preferred amination process is carried out where the hydrogen is present in an amount wherein the hydrogen to ammonia and/or amine molar ratio is greater than 0.01 and preferably less than the ratio 1.0. More preferably, hydrogen is provided in an amount of at least about 0.5 mole percent based on the total moles of ammonia and/or amine, most preferably this percentage is between about 1.0 and about 10 percent. Advantageously, catalysts of the invention operate well at lower hydrogen concentrations based on total feed than do commercially available catalysts for reductive amination. Therefore, the supercritical state can be obtained at convenient pressure.

The amination reaction feed stream optionally also contains an amount of water. The water is often that produced when the starting material polyether derivative is aminated. The water content in the amination feed stream optionally ranges between 0 weight percent and about 10 or more weight percent, based on the weight of the amination feed stream; preferably the water content is kept between about 0 and about 5 weight percent, based on the total weight of the amination feed stream.

Inert gases are also optionally supplied to the reaction such as nitrogen, helium, methane, and the like. Such inert gases are optionally used to help control the reaction temperature and assist in maintaining a desired pressure.

Processes of the invention are preferably conducted in a continuous manner more preferably with a reactor feed being passed through a bed of particulate catalyst. The reactor is optionally an up-flow or down-flow reactor and optionally has a fluidized bed or, more commonly, a fixed bed. The catalyst bed optionally contains inert particles which are, for instance, interspersed throughout the bed and/or form discrete layers, e.g., at an end or intermediary to the bed. Preferably, flow through a catalyst bed is substantially plug flow.

The reductive amination process of the invention is suitably carried out in any equipment having heating means. The process is optionally carried out continuously or in batch. In continuous equipment no agitating means is required because the nature of the continuous process causes the reactants to continually flow in intimate contact with the catalyst material. Agitating means is, however, advantageous in batch processes.

The polyetheramine product compositions from practice of the invention are optionally subjected to separation techniques within the skill in the art for recovering individual components or fractions of the compositions. Illustrative techniques are disclosed in U.S. Pat. No. 5,196,588 (Burgess et al.), U.S. Pat. No. 4,400,539 (Gibson, et al.), U.S. Pat. No. 4,404,405 (Winters), and U.S. Pat. No. 3,151,115 (Moss, et al.).

Polyetheramine derivatives conveniently produced by the process of the invention include amine capped polyols useful in polyurethanes, epoxy resins, fuel and lubrication additives applications, in detergent applications and the like.

The polyetheramines are particularly useful as fuel and lubricant additives because of their solubility therein and the advantageous cleaning effects on fuel injectors. Thus, they are particularly useful in gasoline and other fuels for engines having fuel injectors. Application of ammonia and primary amine capped polyethers as fuel additives is within the skill in the art and explained by Rath et al in U.S. Pat. No. 5,112,364 which is incorporated herein by reference in its entirety.

The present invention unlike the teachings of Rath et al is applicable to formation of polyethers capped with secondary amines. Preferred among these compounds are those represented by Formulas 1 and 2 supra. These compounds are preferred for use as fuel additives because of their surprising solubility when dissolved in fuels. They have other surprising properties of thermal stability and advantageous cleaning effects on fuel system.

The following examples are to illustrate this invention and not limit it. Ratios, parts, and percentages are by weight unless otherwise stated.

Amination or conversion is used to indicate mole percent of reactant product or by-product. It is important to maintain a high percent of amination, preferably above about 5, more preferably above about 50, most preferably about 70 mole percent for the desired product.

EXAMPLE I

ILLUSTRATING THE EFFECTS OF SUPERCRITICAL CONDITIONS IN AMINATION WITH A CATALYST CONTAINING Ni/Co/Cu/Re/B

Preparation of Catalyst—A hot solution containing 118 gm $Ni(NO_3)_2 \cdot 6H_2O$, 10.2 gm $NH_4ReO_4$, 29.5 gm $H_3BO_3$ and 34.5 g. $Co(NO_3)_2 \cdot 6H_2O$, and 25.6 gm of $Cu(NO_3)_2 \cdot 2.5H_2O$ in 400 ml of distilled water was prepared. Fifty gm of predried catalyst support (an alumina support commercially available from U.O.P. under the trade designation SAB-17™) was placed in a 500 ml round bottom flask under vacuum. Then 200 ml of the catalyst solution was added to the support. After thorough mixing, the impregnated support was re-dried at 120° C. for 2 hour and impregnated as described above with a second batch of the 200 ml catalyst solution. The completely impregnated support was dried again at 120° C. for 2 hour, calcined at 300° C. in a furnace for 3 hours.

The resulting catalyst contains a Ni/Co/Cu/Re/B metal weight ratio of 48/14/14/14/10 and the Ni/Co and Ni/Cu weight ratios are 3.4. The total metal loading is about 50 weight percent.

Activation of Catalyst—The catalyst was loaded into a tubular activation chamber with a stream of pure $H_2$ flow (450 ml/min.) evenly through the entire catalyst bed. Temperature inside the chamber was gently heated up and hold it at 320°±15° C. for 3 hours. Then the heat was turned off and the catalyst was allowed to cool under continuous hydrogen flow. The activated catalyst (total metal loading= 50 weight percent) was then stored in a nitrogen filled dry box until use.

Plug-Flow Reactor Evaluation—Loading of the catalyst (44 g/75 ml) into a plug-flow having dimensions of 1 inch (25.4 mm) inside diameter and 100 mL capacity, commercially available from Autoclave Engineer rated at 9500 psi (65500 kPa)/5500° F. (260° C.) reactor, is performed inside a $N_2$ filled drybox ($O_2$ less than 10 ppm) to prevent deactivation of the catalyst. Ceramic beads packing (⅛") is used above and below the catalyst so the catalyst bed is positioned in the constant temperature zone of the reactor.

The catalyst was maintained at a constant temperature of from 180°–210° C., and a pressure of from 1200 to 3000 psig 8273 to 20684 kpag).

The flow rates are 0.2–1.0 ml/min. for polyol (a polybutylene based polyether polyol prepared from butylene oxide, having a molecular weight of about 1500 and one hydroxyl group per molecule), 0.11–0.54 ml/min. for amines (isopropyl amine (IPA) and diisopropyl amine (DIPA), 2–193 sccm (standard cubic centimeters per minute) for $H_2$ which results a amine/OH molar ratio of 2–11, a total mole of 2–86% $H_2$ and LHSV (liquid hourly space velocity) of 0.16–0.8. (LHSV=volume of polyether polyol/volume of catalyst bed/hour) The results are summarized in Table 1. Excess amine (IPA & DIPA) and/or ammonia is removed from polyol product by vacuum at 70° C. The final product is analyzed by acid titration and by carbon-13 NMR spectrometer (Bruker 250 MHz).

TABLE 1

| Sample # | Catalyst | Temp. (C.) | Polyol ml/min | Isopropyl-A ml/min (IPA) | H2 sccm | Pressure (psig)* | Amination % | Amine/OH | % H2 | LHSV |
|---|---|---|---|---|---|---|---|---|---|---|
| A25 | NiReBCoCu | 180 | 1.0 | 0.26 | 193 | 1200 | — | 5 | 70% | 0.80 |
| B25 | 50 wt. %, 44 g/75 ml | 200 | 1.0 | 0.26 | 193 | 1200 | 6% | 5 | 70% | 0.80 |
| C25 | 1/16", SAB-17 | 210 | 0.4 | 0.21 | 193 | 1200 | 11% | 4 | 76% | 0.32 |
| D25 | | 210 | 0.2 | 0.11 | 193 | 1200 | 9% | 2 | 86% | 0.16 |
| E25 | | 210 | 0.2 | 0.11 | 193 | 2100 | 4% | 2 | 86% | 0.16 |
| F25 | | 210 | 0.2 | 0.11 | 30 | 2100 | 5% | 2 | 49% | 0.16 |
| G25 | | 210 | 0.2 | 0.11 | 10 | 2400 | 52% | 2 | 24% | 0.16 |
| H25 | | 210 | 0.2 | 0.11 | 0 | 2400 | 78% | 2 | 24% | 0.16 |

| | Catalyst | Temp. (C.) | Polyol ml/min | Diisop-Am (DIPA) ml/min | H2 sccm | Pressure (psig) | Amination | Amine/OH | % H2 | LHSV |
|---|---|---|---|---|---|---|---|---|---|---|
| A27 | NiReBCoCu | 200 | 0.6 | 0.54 | 30 | 2400 | 18% | 11 | 24% | 0.48 |
| B27 | 50 wt. %, 44 g/75 ml | 200 | 0.6 | 0.64 | 30 | 2400 | 7% | 11 | 24% | 0.48 |
| C27 | 1/16", SAB-17 | 209 | 0.6 | 0.54 | 2 | 2400 | 38% | 11 | 2% | 0.48 |
| D27 | | 209 | 0.2 | 0.18 | 2 | 2400 | 100% | 4 | 6% | 0.16 |
| E27 | | 203 | 0.2 | 0.18 | 2 | 2400 | 70% | 4 | 6% | 0.16 |
| M27 | | 209 | 0.2 | 0.18 | 2 | 3000 | 100% | 4 | 6% | 0.16 |
| N27 | | 200 | 0.2 | 0.18 | 2 | 3000 | 100% | 4 | 6% | 0.16 |
| O27 | | 200 | 0.4 | 0.36 | 2 | 3000 | 57% | 7 | 3% | 0.32 |
| P27 | | 200 | 0.4 | 0.36 | 2 | 3000 | 4% | 7 | 3% | 0.32 |

*1200 psig = 8,274 kPag
2100 psig = 14,479 kPag
2400 psig = 16,550 kPag
3000 psig = 20,688 kPag The data in Table 1 show that comparative samples A25–F25 wherein supercritical phase conditions are not achieved give poor yields of products; whereas supercritical conditions in G25 and H25 result in high yield of polyetheramine. In these examples supercritical conditions are reached by increasing the temperature to 209° C.–210° C., increasing pressure to 2400 psig (16,500 kPag), and decreasing the hydrogen concentration to 24–86 mole percent.

In the series A27–C27 and Examples D27–O27, the hydrogen amount is maintained very low while the pressure is high. The temperature is reduced to 200° C. to avoid degradation. It is surprising that the catalyst, the preferred catalyst having Ni/Re/B/Co/Cu is effectively active at such a low (e.g. 6–24 mole percent) hydrogen level, which hydrogen level is important to obtain supercritical conditions at temperatures sufficiently low to avoid degradation.

We claim:

1. A process for producing polyetheramine products by the catalytic amination of polyether derivatives, said method comprising contacting said polyether derivatives with ammonia and/or reactant amine under supercritical conditions in the presence of hydrogen and a reductive amination catalyst said reductive amination catalyst comprising nickel, rhenium, cobalt, copper and boron.

2. The process of claim 1 wherein the temperature is from about 120° C. to about 500° C.

3. The process of claim 1 wherein the polyether derivatives have from about 6 to about 500 carbon atoms and at least one functional group capable of being replaced by an amine group.

4. The process of claim 3 wherein each functional group capable of being replaced by an amine group is independently selected from hydroxy groups, aldehyde, ketone, imino groups and combinations of said groups.

5. The process of claim 4 wherein the temperature is about 200° C. or less.

6. The process of claim 1 wherein the polyether derivative is a polyalkylene glycol; polyalkylene glycol derivative including one initiated with a phenol; pyrrolidine or other aromatic compound; polyoxyalkylene alcohol; and their derivatives and mixtures thereof.

7. The process of claim 1 wherein the polyetheramine is of Formula 1 or Formula 2:

Formula 1

Formula 2 where R1 is a hydroxyalkylpolyether, hydroxyarylpolyether or hydroxyalkylarylpolyether radical of the general formula

Formula 3a wherein Ar is any aromatic moiety, having at least one aromatic ring or a alicyclic polyether or alkylalicyclic polyether of the general formula:

Formula 4a where Cy represents any cyclic structure of at least about 4 atoms; $R^2$ and $R^3$ may be identical or different and are each alkyl, alkylamine, alkyldiamine, or alkylenepolyamine of 1 to about 20 carbon atoms; $R^4$ is an anion; $R^5$, $R^6$ and $R^7$ may be identical or different and are each hydrogen, hydroxyl, carbonyl, ketone or a hydrocarbon radical of 1 to about 30 carbon atoms. $R^8$ is a polyether chain obtained from an alkylene oxide of 2 to about 8 carbon atoms or a mixture of such alkylene oxides, having from 2 to about 100 alkylene oxide units in the chain.

8. The process of claim 7 wherein Ar is selected from 1,3 diazoles, pyrazoles, pyrazines, pyrimidines, pyridazines, purines, pteridines, thiophenes, oxazones, pyridines, dihydroquinolines, benzoquinolines, diazaanthracenes, naphthalenes, phenyl groups (benzene rings), and combinations thereof, or Cy is selected from cyclohexane, furan, tetrahydrofuran, dioxolane, pyran, tetrahydropyran, dioxepin, azetidine, dihydropyroles, pyrrolidine, pyrroline, pyrrolidinone, cyclic lactams of from about 5 to about 7 cyclic atoms (preferably from about 4 to about 6 carbon atoms and one nitrogen atom in the ring), and combinations thereof.

9. The process of claim 1 wherein the polyether is an arylpolyether and each cyclic structure of the arylpolyether derivative has from about 5 to about 7 carbon atoms and at least one functional group capable of being replaced by an amine group.

10. The process of claim 9 wherein each functional group is independently selected from hydroxy groups, aldehydes, ketones, imino groups and combinations of said groups.

11. The process of claim 9 wherein each arylpolyether derivative has from about 6 to about 500 carbon atoms.

12. The process of claim 11 wherein the arylpolyether derivative is selected from aryl ethers, polyarylether polyols, aryl methyl ethers, aryl ethyl ethers, aryl propyl ethers, aryl butyl ethers, aryl pentyl ethers, aryl, and combination thereof.

13. The process of claim 11 wherein the aryl groups each have from about 5 to about 30 carbon atoms.

14. The process of claim 13 wherein the aryl groups each have from about 6 to about 12 carbon atoms.

15. The process of claim 14 wherein each aryl group is independently selected from phenyl, or substituted phenyl including methylphenyl, dimethylphenyl, trimethylphenyl, ethylphenyl, diethylpheny, methyl ethylphenyl, propylphenyl, methoxyphenyl, and ethoxyphenyl.

16. The process of claim 1 wherein the polyether derivative is reacted with at least one amine.

17. The process of claim 16 wherein the amine is a primary or secondary amine.

18. The process of claim 17 wherein the amine is a secondary amine.

19. The process of claim 18 wherein the amine has from 1 to about 10 carbon atoms and from 1 to about 10 nitrogen atoms.

20. The process of claim 19 wherein the amine has from 1 to about 6 carbon atoms and from 1 to about 6 nitrogen atoms.

21. The process of claim 17 wherein the amine comprises methyl amine, ethylamine, propylamine, butylamine, ethylenediamine, aniline, piperazine, aminoethylpiperazine, diethylenetriamine, triethylenetetraamine, tetraethylenepentaamine, pentaethylenehexaamine, diethylamine, dipropylamine, dibutylamine, isopropylamine, diisopropylamine, diisopropanolamine, ethanolamine, diethanolamine, diisobutyleneamine and combinations thereof.

22. The process of claim 21 wherein the amine reacts with an arylpolyether derivative selected from aryl ethers, polyarylether polyols, aryl methyl ethers, aryl ethyl ethers, aryl propyl ethers, aryl butyl ethers, aryl pentyl ethers, aryl, and combinations thereof.

23. The process of claim 1 wherein the amination occurs at sufficient pressure to maintain desired amounts of hydrogen and ammonia and/or amine present at a desired temperature in a supercritical phase.

24. The process of claim 23 wherein the pressure is at least about 20 atmospheres (2026 kPa) and no greater than about 400 atmospheres (40,530 kPa).

25. The process of claim 24 wherein the pressure is at least about 1800 psig (12413 kPa).

26. The process of claim 24 wherein the temperatures are at least about 120° C. and less than about 250° C.

27. The process of claim 26 wherein the temperature is from about 150° C. to about 210° C.

28. The process of claim 27 wherein the temperature is from about 180° to about 210° C. and the pressure is from about 2000 to about 4000 psig (13790 to 27579 kPa).

29. The process of claim 1 wherein the polyether derivative reacts with both ammonia and an amine.

30. The process of claim 29 wherein the amine comprises diisopropylamine and/or isopropylamine.

31. The process of claim 1 wherein the molar ratio of amine to total polyether derivative is from at least about 1:1 to about 50:1.

32. The process of claim 31 wherein the molar ratio of amine to total polyether derivative 1:1 to about 12:1.

33. The process of claim 1 wherein the hydrogen to amine molar ratio is greater than 0.01 and less than 1:1.

34. The process of claim 33 wherein the hydrogen to amine molar ratio is from about 0.02 to about 0.1.

35. The process of claim 1 wherein the catalyst is used in an amount of at least about 10 lb/ft$^3$ (160/m$^3$).

36. The process of claim 35 wherein the catalyst is used in an amount of at less than about 150 lb/ft$^3$ (2400 kg/m$^3$).

37. The process of claim 1 wherein the amine product is at least one polyamine useful in polyurethanes, epoxy resins, detergent, corrosion inhibitor, dispersant, defoamers, or fuel or lube oil additive applications, amine functional chelating compounds useful in detergent applications or combination thereof.

38. The process of claim 37 wherein the amine product has at least one other functional group.

39. The process of claim 1 wherein the liquid hourly space velocity based on the total feed and volume of reactor containing catalyst is at least about 0.05 reciprocal hours and no greater than about 2 reciprocal hours.

40. The process of claim 1 wherein the reductive amination catalyst further comprises ruthenium.

* * * * *